United States Patent [19]

Taylor

[11] Patent Number: 5,157,457
[45] Date of Patent: Oct. 20, 1992

[54] CALORIMETRIC FIBER OPTIC CHEMICAL SENSOR

[75] Inventor: Henry F. Taylor, College Station, Tex.

[73] Assignee: The Texas A&M University System, College Station, Tex.

[21] Appl. No.: 592,501

[22] Filed: Oct. 3, 1990

[51] Int. Cl.⁵ .............................................. G01B 9/02
[52] U.S. Cl. ........................... 356/345; 250/227.19; 356/352; 356/361
[58] Field of Search ............... 356/345, 349, 360, 361, 356/352, 133; 250/227.19; 525/329.4

[56] References Cited

U.S. PATENT DOCUMENTS

| | | | |
|---|---|---|---|
| 4,663,961 | 5/1987 | Nelson et al. | 73/24 |
| 4,792,689 | 12/1988 | Peterson | 250/458.1 |
| 4,801,655 | 1/1989 | Murray, Jr. et al. | 525/329.4 |
| 4,817,101 | 3/1989 | Wyeth et al. | 356/349 |
| 4,824,206 | 4/1989 | Klainer et al. | 350/96.29 |
| 4,827,121 | 5/1989 | Vidrine, Jr. et al. | 250/227 |
| 4,842,783 | 6/1989 | Blaylock | 264/1.4 |
| 4,846,548 | 7/1989 | Klainer | 350/96.29 |

Primary Examiner—Samuel Turner
Assistant Examiner—LaCharles P. Keesee
Attorney, Agent, or Firm—Arnold, White & Durkee

[57] ABSTRACT

The present invention is directed to a sensor which utilizes an optical fiber interferometer to detect the absorption of a modulated laser beam by a particular chemical species. In particular, one embodiment of the present invention comprises a fiber optic system in which light from a continuously operating laser is modulated prior to passing through a region containing a chemical species of interest. Absorption of the light from the laser causes heating of the chemical species which, in turn, emits thermal energy that is transferred to an optical fiber that is situated in close proximity to the region in which the light is absorbed. In turn, the increase of the temperature of the optical fiber results in a change in the fiber's refractive index, thereby resulting in a change in the transmittance of said interferometer. The change in transmittance of the fiber is converted into an electrical signal in a photodetector. Thereafter, the modulated signal from the photodetector is recovered by phase-sensitive detection, using a lock-in amplifier. In this fashion, the amplitude of the output signal from the amplifier is proportional to the amount of light absorbed by the chemical species of interest. The concentration of this chemical species may thus be determined.

32 Claims, 3 Drawing Sheets

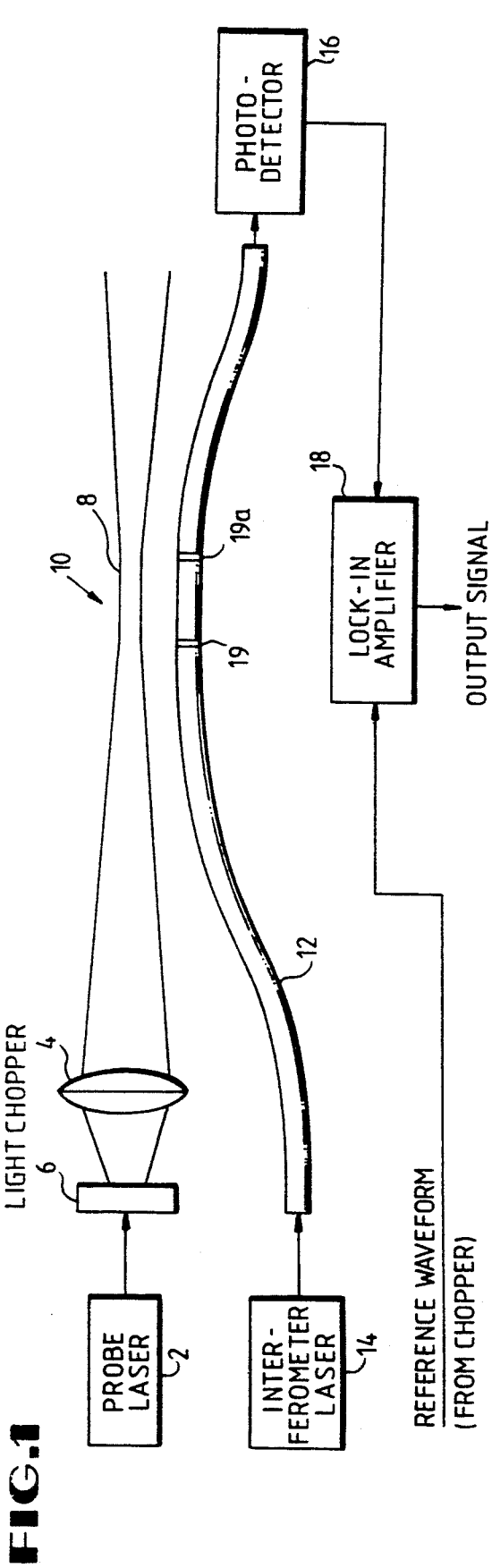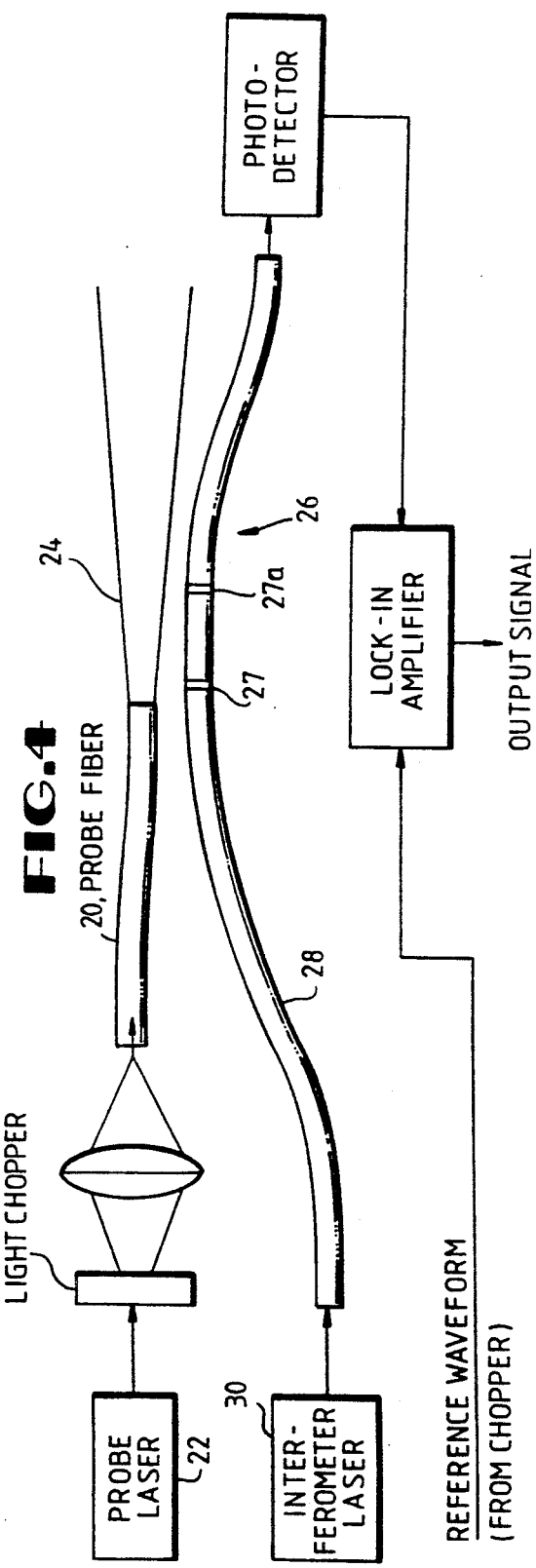

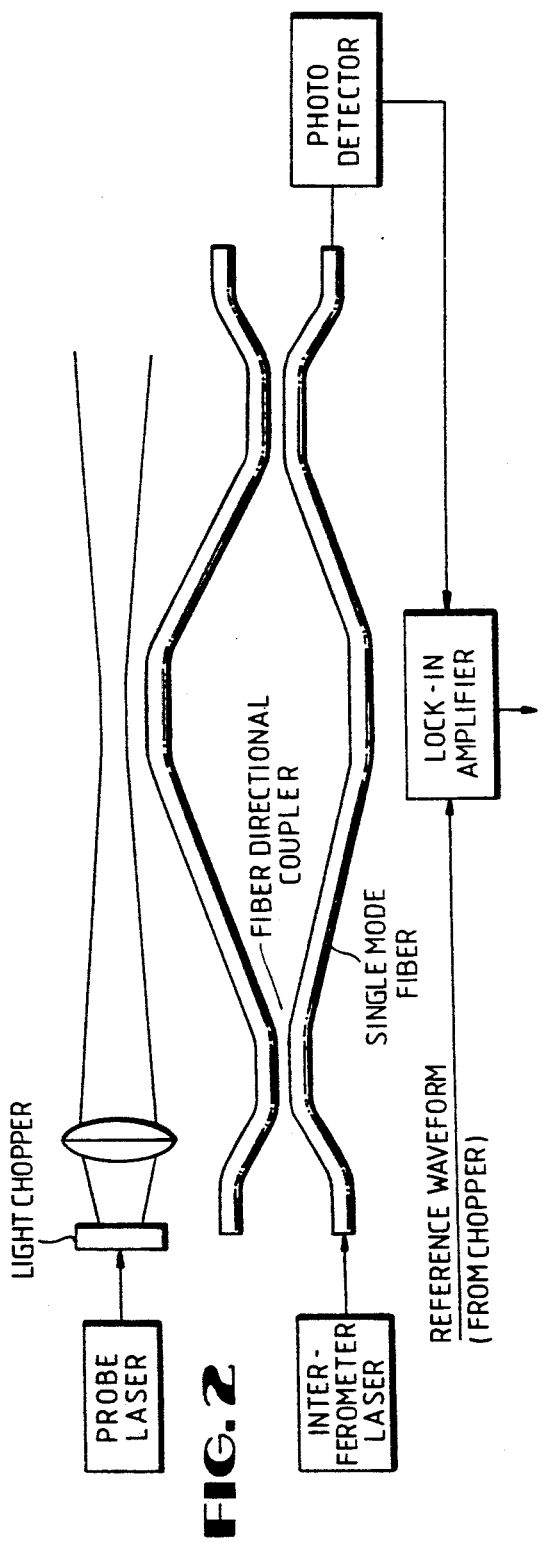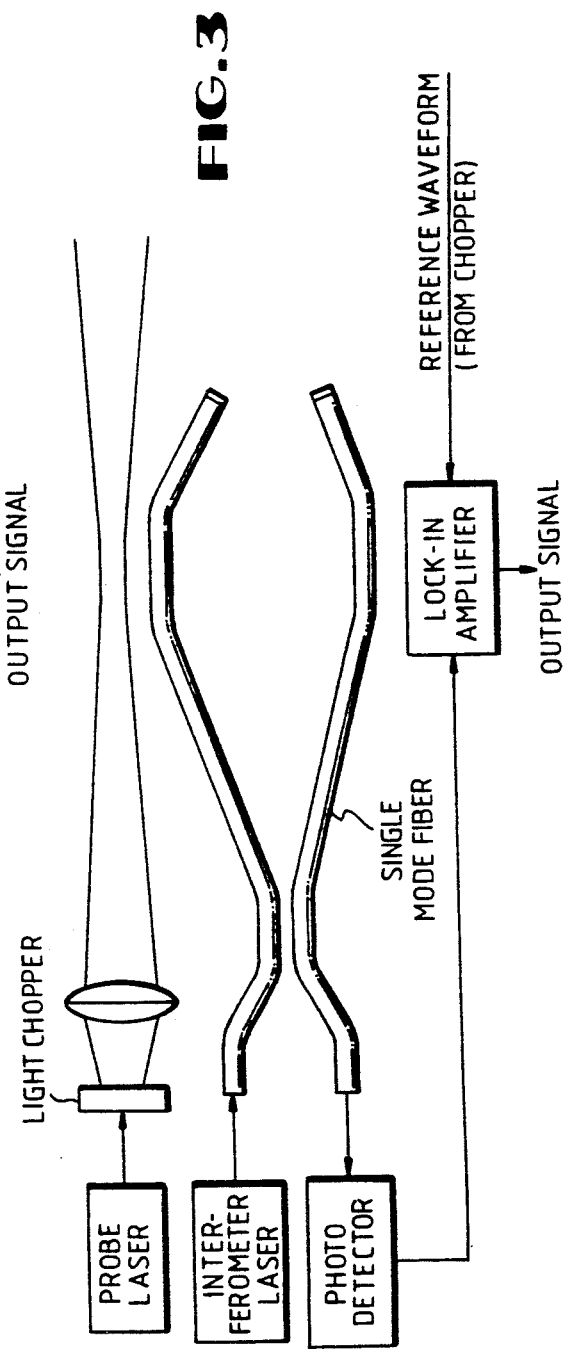

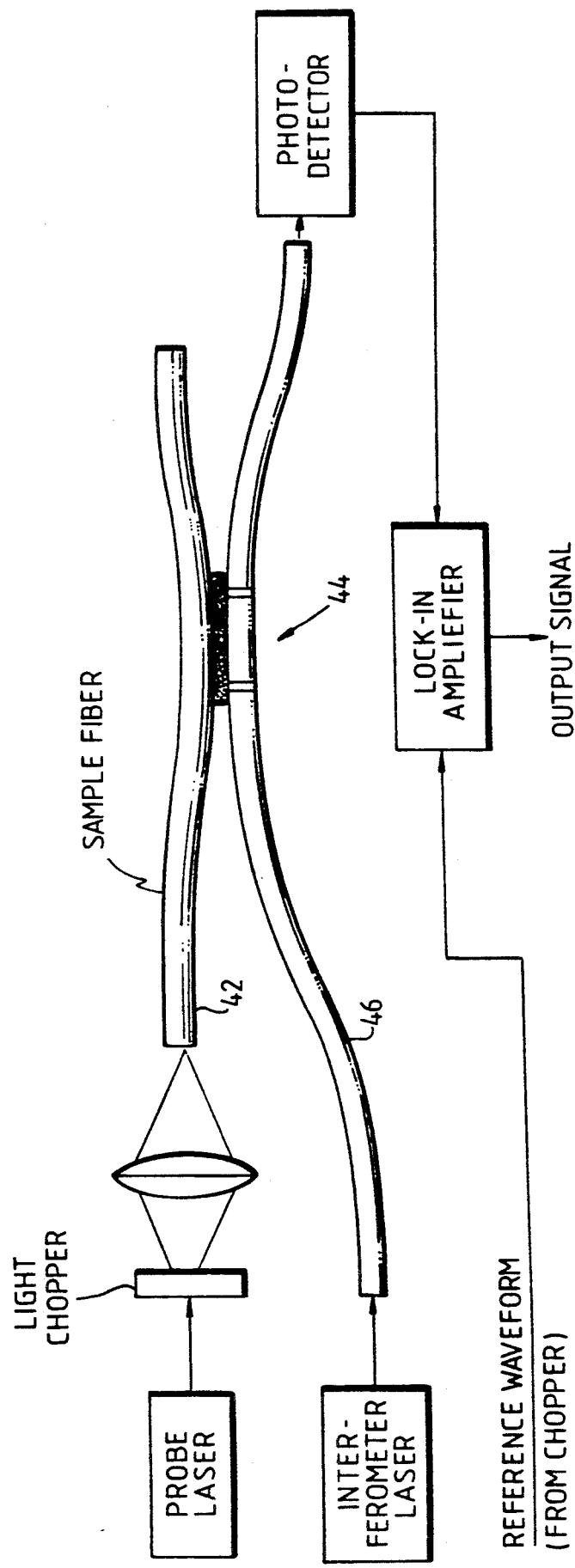

CALORIMETRIC FIBER OPTIC CHEMICAL SENSOR

The U.S. Government has rights in this invention pursuant to Grant No. ECS-8716880, with the National Science Foundation.

BACKGROUND OF THE INVENTION

1. Field of the Invention

The present invention is generally related to a method and apparatus for performing quantitative analysis of certain chemical species in the gaseous, liquid, or solid state. More specifically, the present invention is directed to a sensor which utilizes an optical fiber interferometer to detect the absorption of a modulated laser beam by a particular chemical species. The present invention is also directed to a means and method to monitor optical absorption in an optical fiber.

2. Description of the Prior Art

Fiber optics have, in many ways, supplanted metal conductors as the favored information transfer medium choice for both science and industry. In this connection, fiber optics have been widely employed in a variety of telecommunication applications. Fiber optics have also been utilized in sensitive sensor systems such as those disclosed in Applicant's U.S. copending application Ser. No. 286,058, which is herein incorporated by reference.

Fiber optic sensor systems are attractive for a number of reasons including immunity to electromagnetic interference, ability to operate in a wide variety of environments, high sensitivity, and the potential for multiplexing. Chemical sensors incorporating fiber optics have generally utilized "optrodes" or materials which undergo changes in optical properties when interacting with a chemical of interest. The optrode is usually deposited on the end of the fiber. When chemically acted upon, the chemical reaction affects the fluorescence properties of the optrode as well as its reflectance or transmittance.

The use of optrodes, however, has not gained widespread practical application. This is believed to be due in part to the relatively slow response times of optrodes which is usually measured in term of minutes. Furthermore, optrodes generally show relatively low sensitivity and nonlinear response characteristics which change over extended time periods of use. Additionally, each optrode generally can only be used to detect one chemical species.

SUMMARY OF THE INVENTION

The present invention addresses the aforementioned disadvantages of prior art chemical and biological detection systems by providing a calorimetric sensing system and process which enables rapid response, high sensitivity, linearity, and the ability to measure concentrations of multiple chemical species in a simultaneous fashion. The calorimetric sensor of the present invention also has application as a photodetector.

A fundamental feature of the calorimetric sensor described herein is the use of an optical fiber interferometer to sense a temperature change produced in a chemical species by absorption of light of a selected wavelength. A portion of the heat produced in said chemical species by said absorption of light is transferred to said optical fiber by conduction, convection, or diffusion. The resultant heating of the fiber causes a change in the optical transmissivity of the fiber interferometer. Measurement of this transmissivity change allows the concentration of a particular constituent of the chemical species to be determined.

One embodiment of the present invention comprises a fiber optic system in which light from a continuously operating laser is modulated prior to passing through a region containing a chemical species of interest, or perhaps a chemical impurity. This chemical species selectively absorbs light at the frequency emitted by the laser. The wavelength of the modulated light beam is chosen to coincide with a wavelength at which light is absorbed by the impurity or chemical species. The wavelengths and strengths of absorption peaks of most of the chemical species of interest are set forth in the literature. Absorption of light from the laser causes heating of the chemical species which omits thermal energy which is diffused into the surrounding medium. Some of this thermal energy is transferred to an optical fiber which is situated in close proximity to the region in which light is absorbed. The influx of thermal energy causes a temperature increase in the optical fiber, which increase results in a change in the fiber's refractive index via the thermo-optic effect. The fiber is part of an interferometer, and the refractive index change results in a change in the transmittance of said interferometer. This change in transmittance causes a change in the optical power from a second laser which is converted to an electrical signal by a photodetector after passing through said interferometer. The electrical signal from the photodetector may then be processed. Several types of optical fiber interferometer can be used in the calorimetric sensor, including Fabry-Perot, Mach-Zehnder, and Michelson interferometers.

Such a system as described has application in monitoring atmospheric concentrations of such chemicals as propane or methane, in monitoring the concentration of constituents such as oxygen in human blood, and in monitoring the concentrations of impurities such as iron in solid glasses.

A second embodiment of the invention comprises the use of an optical fiber to transmit light from a first laser to an interaction region near a fiber optic interferometer as previously described. This embodiment can be used in a catheter for biomedical monitoring. A third embodiment of the invention is directed to a system to monitor the optical absorption of a solid glass fiber which is in thermal contact with the fiber optic temperature sensor.

The present invention has a number of advantages over prior art chemical sensing systems. One such advantage is the speed at which a chemical response can be evaluated. In comparison to previous systems which require minutes to evaluate a response, a response is generally produced in the present system in one second or less.

The present invention also demonstrates an enhanced sensitivity. In this connection, the present invention allows the detection of parts per million concentrations of gases such as methane, $\mu$mole concentrations of liquid dyes such as coumarin, and fiber attenuations as low as 0.1 dB/km. The present system also exhibits linear response characteristics which are significant from the standpoint of precise quantitative determination of the concentration of chemical species of interest.

Finally, the present invention enables the detection of the concentrations of multiple chemical species in a simultaneous fashion. This is accomplished using a single light source which can be tuned in wavelength, or multiple light sources operating at different fixed wavelengths. This is significant because one sensor can perform the same function as several sensors which can detect only a single chemical species (as in the case of "optrodes" for example).

Other objects, features, and advantages of the invention will become more apparent upon reference to the following specification and drawings.

BRIEF DESCRIPTION OF THE DRAWINGS

FIG. 1 illustrates a schematic diagram of a fiber optic chemical sensor using a Fabry-Perot interferometer for temperature sensing.

FIG. 2 illustrates a schematic diagram of a fiber optic chemical sensor with a Mach-Zehnder interferometer for temperature sensing.

FIG. 3 illustrates a schematic diagram of a fiber optic chemical sensor with a Michelson interferometer for temperature sensing.

FIG. 4 illustrates a schematic diagram of a fiber optic chemical sensor with a fiber probe input.

FIG. 5 illustrates a schematic diagram of a sensor for fiber attention measurement.

DETAILED DESCRIPTION OF PREFERRED EMBODIMENT

A schematic diagram of one embodiment of a fiber optic chemical sensor of the present invention is illustrated in FIG. 1. Modulated light from a probe laser 2 is transmitted through a focusing means 4 such as a convex lens. In instances where a continuously operating probe laser is used, e.g., a helium neon laser, modulation of the transmitted light may require the use of a light chopper 6 such as one manufactured by Oriel Manufacturing Co. In instances where a semiconductor laser is used, modulation of the transmitted light beam may be accomplished by varying the current to the laser itself. Typical values of the frequency at which the light is modulated preferably lie in the range between 1 Hz and 1000 Hz. Modulated light from laser 2 is passed through focusing means 4 so as to produce a narrow waist of light 8 passing through an interaction region 10 containing the chemical of interest. For purposes of discussion, the term "interaction region" 10 will be used herein to describe that area in which a modulated focused light beam is propagated through the chemical species, whether said chemical is found in a gaseous, liquid or solid medium. Preferably, this focusing is done in a gradual fashion so as to produce a relatively long beam of narrow cross section.

The optical power emitted by laser 2, and transmitted through the region 10 in which the chemical is present, is modulated at a fixed frequency f so that light absorbed by the chemical produces a temperature change which varies in time at this frequency f. The thermal energy is diffused into the surrounding media which may be gaseous, liquid, or solid. To evaluate the absorption of this light energy, a single mode optical fiber 12 is placed outside but immediately proximate to the interaction region 10. Typical values for the proximity between the interaction region 10 and optical fiber 12 are in the order of 0.001 to 1.0 mm, as determined by thermal diffusion rates of the medium in which the chemical is dispersed. As a result of the transfer of heat energy by means of thermal diffusion, conduction, or convection, the single mode fiber is heated such that its temperature also varies at a frequency f.

Optical fiber 12 is coupled to an interferometer laser 14, e.g. a semiconductor laser, such that light from laser 14 is transmitted through said fiber. The second end of fiber 12 is coupled to a conventional photodetector 16, such as a Mitsubishi Model PD 7001 indium gallium arsenide photodiode. Optical fiber 12 is provided with two mirrors 19 and 19A which define the cavity of a Fabry-Perot interferometer of FPI. On average, mirrors 19 and 19A are separated by a distance in the order of a few millimeters to a few centimeters. As disclosed in Applicant's U.S. Pat. No. 4,923,273 and pending applications Ser. Nos. 286,055 and 286,058, and also described by Lee, Atkins, and Taylor in "Performance of a Fiber-Optic Temperature Sensor From −200 ° to 1050° C." which appeared in Optics Letters, Vol. 13, pp. 1038-1040 (November 1988), this type of interferometer may operate as an extremely sensitive temperature sensor. Accordingly, a small temperature change in fiber 12 in the region between mirrors 19 and 19A can lead to a substantial change in the amount of light from laser 14 which is transmitted through fiber 12 to photodetector 16.

When interferometer laser 14 is operated in a continuous fashion, the output signal from photodetector 16 will vary at a frequency f corresponding to the modulation frequency f of probe laser 2. In a preferred embodiment, the amplitude of the modulated signal from photodetector 16 is recovered by phase sensitive detection using a lock-in amplifier 18, such as an Ithaco Model 3961B Lock-in amplifier. In this fashion, the lock-in amplifier 18 serves as a noise discrimination device. The amplitude of the output signal from the lock-in amplifier 18 is proportional to the amount of light absorbed by the chemical species of interest. The concentration of this chemical species may be thus determined.

One application of the aforedescribed embodiment is in the monitoring of methane or propane concentrations in the atmosphere. Light at the 3.39 $\mu$m helium neon laser wavelength is strongly absorbed by both gases. Light at various carbon dioxide laser lines with wavelengths near 10 $\mu$m is also selectively absorbed by a number of other commonly encountered gases, including ammonia, ozone, benzene, and vinyl chlorides. This phenomenon is described by K. A. Fredriksson in "Differential Absorption for Pollution Monitoring" as appearing in Laser Remote Chemical Analysis, pp. 303–304 (R. M. Measures, ed., Wiley, N.Y., 1988). The aforedescribed sensor system also has application to monitor concentrations of colored species, e.g., dyes dissolved in water or other liquids, or oxygen concentrations in human blood. A second configuration for the sensor utilizing a Mach-Zehnder interferometer is illustrated in FIG. 2. A third configuration for the sensor utilizing a Michelson interferometer is illustrated in FIG. 3.

A second embodiment of the present invention may be seen by reference to FIG. 4. FIG. 4 illustrates the use of a probe optical fiber 20 adapted to carry light transmitted by a probe laser 22 to an interaction region 24 near a fiber optic temperature sensor 26 similar to that earlier described in association with the embodiment illustrated in FIG. 1. Conventional fused fibers made of doped silica $SiO_2$ may be used in the probe fiber 20 for wavelengths from about 0.25 $\mu$m to 2.0 $\mu$m. Fluoride or chalcogenide glass fibers are preferred for wavelengths longer than about 2.0 $\mu$m. As described in connection with the first embodiment, a single mode silica fiber may be used for the interferometer fiber 28 which is coupled to a second laser 30 and photodetector 32 as illustrated in FIG. 4. The interferometer fiber 28 is provided with a pair of mirrors 27 and 27A so as to define a Fabry-Perot interferometer. In such a fashion, heat sensitivity may be measured in a fashion as earlier described.

The embodiment illustrated in conjunction with FIG. 4 may be adapted for use in a catheter which can be inserted into a blood vessel for biomedical monitoring. Such a sensor could also be deployed in a building or compartment for monitoring of the concentration of hazardous fumes or in a liquid medium being processed chemically. It should also be recognized that a probe fiber, as in FIG. 4, can be used with other interferometer configurations; in particular, the Mach-Zehnder interferometer of FIG. 2 or the Michelson interferometer of FIG. 3.

FIG. 5 illustrates a third embodiment of the present invention which represents an arrangement for monitoring optical absorption at the wavelength of a continuously operating probe laser 40 in a solid glass sample fiber 42. This embodiment incorporates many of the features discussed in association with the embodiment of FIGS. 1-3. In the illustrated embodiment, thermal diffusion from a sample fiber 42 to the temperature sensor 44 of the interferometer fiber 46 occurs via a fastening agent, e.g., epoxy 49, which joins the two fibers. Attenuation measurements of this type have utility in the development of new generations of low loss optical fibers, particularly those designed for infrared applications. In particular, fluoride and chalcogenide glasses which are being developed for telecommunications and biomedical applications could be evaluated for optical absorption in this manner.

What is claimed is:

1. A fiber optic chemical sensor comprising:
   a probe laser light source adapted to emit a light beam through an interaction zone containing a given chemical species;
   means to modulate said beam at a set frequency f so as to induce a temperature change in said chemical species variable at said frequency f;
   an optical fiber coupled at one end to an interferometer laser light source, where said optical fiber is provided with two mirrors arranged in serial fashion along its length so as to define a Fabry-Perot cavity, where said cavity is situated adjacent to the interaction zone; and
   a photodetector coupled to the second end of said fiber remote from said second laser light source and receptive to light emitted from said second source through said Fabry-Perot cavity so as to enable detection of heat diffused by said chemical specie in said interaction zone.

2. The fiber optic chemical sensor of claim 1 wherein the separation between the interaction zone and the Fabry-Perot cavity is in the range of 0.001 to 1.0 mm.

3. The fiber optic chemical sensor of claim 1 wherein the modulation frequency f is in the range of between 1 Hz and 1000 Hz.

4. The fiber optic chemical sensor of claim 1 further including means to focus the modulated light prior to passing through said interaction zone.

5. The fiber optic chemical sensor of claim 1 wherein light modulation is accomplished via a light chopper.

6. The fiber optic chemical sensor of claim 1 wherein light modulation is accomplished by varying the current to the probe laser light source.

7. The fiber optic chemical sensor of claim 1 wherein the mirrors of the Fabry-Perot cavity are spaced in a range 1 mm-10 cm apart.

8. The fiber optic chemical sensor of claim 1 further including a lock-in amplifier coupled to said photodetector and adapted to receive said modulated signals from said photodetector.

9. The fiber optic chemical sensor of claim 1 in which the interferometer laser is a semiconductor diode laser.

10. The fiber optic chemical sensor of claim 1 in which the interferometer is a Mach-Zehnder interferometer.

11. The fiber optic chemical sensor of claim 1 in which the interferometer is a Michelson interferometer.

12. A chemical sensor comprising:
   probe laser adapted to emit a light beam through a probe fiber to an interaction area containing a selected chemical species in a gaseous, liquid, or solid form such that said light is absorbed by said chemical specie in said interaction area;
   means to modulate the light emitted by said probe laser through said species at a set frequency f so as to induce a temperature change in said chemical species variable at said frequency f;
   a second optical fiber coupled at one end to an interferometer laser, where said optical fiber is provided with two mirrors arranged in serial fashion along its length so as to define a Fabry-Perot cavity, said cavity being situated immediately proximate to said interaction area; and
   a photodetector coupled to the second end of said second fiber opposite said interferometer laser so as to receive light from said interferometer laser propagated through said Fabry-Perot cavity.

13. The chemical sensor of claim 12 further including means to focus said modulated light emitted by said probe laser.

14. The chemical sensor of claim 12 further including a lock-in amplifier or other phase-sensitive demodulation coupled to said photodetector and adapted to receive said modulated signal from said photodetector.

15. The chemical sensor of claim 12 wherein the probe fiber is comprised of $SiO_2$ for optical wavelengths from about 0.25 $\mu$m to 2.0 $\mu$m.

16. The chemical sensor of claim 12 wherein the probe fiber is comprised of fluoride or chalcogenide for optical wavelengths greater than 2.0 $\mu$m.

17. The chemical sensor of claim 12 wherein the interferometer fiber is comprised of a single mode silica fiber.

18. The chemical sensor of claim 12 wherein light modulation is accomplished via a light chopper.

19. The chemical sensor of claim 12 wherein light modulation is accomplished by varying the current supplied to the probe laser.

20. The chemical sensor of claim 13 wherein the means to focus the modulated light comprises a lens.

21. The chemical sensor of claim 12 in which the interferometer laser is a semiconductor diode laser.

22. The chemical sensor of claim 12 in which the interferometer is a Mach-Zehnder interferometer.

23. The chemical sensor of claim 12 in which the interferometer is a Michelson interferometer.

24. An apparatus for fiber attenuation measurement comprising:
   a probe laser adapted to transmit a light beam through a sample fiber, means to modulate the light transmitted by said probe laser, and means to focus said modulated light through said sample fiber;

an interferometer fiber coupled at one end to an interferometer laser, where said interferometer fiber is provided with a series of mirrors along its length so as to define a Fabry-Perot cavity;

a photodetector coupled to the second end of said interferometer fiber opposite said interferometer laser so as to receive light transmitted through said Fabry-Perot cavity; where said sample fiber is coupled in a heat transfer relationship to said interferometer fiber near said Fabry-Perot cavity.

25. The apparatus of claim 24 further including a lock-in amplifier coupled to said photodetector to receive said modulated signal.

26. The apparatus of claim 24 wherein said sample and interferometer fibers are bonded with an epoxy resin.

27. The apparatus of claim 24 wherein the interferometer laser is a semiconductor diode laser.

28. The apparatus of claim 24 wherein the interferometer is a Mach-Zehnder interferometer.

29. The fiber optic chemical sensor of claim 24 wherein the interferometer is a Michelson interferometer.

30. A method to detect the identity and/or presence of a selected chemical, comprising:

situating an interferometer immediately adjacent to a zone where dispersal of said chemical is expected, where said interferometer comprises:

an optical fiber coupled at one end to an interferometer laser, where said optical fiber is provided with two mirrors arranged serially along its length so as to define a Fabry-Perot cavity, and coupled to a photodetector at said second end to receive light propagated through said cavity;

directing light from a probe laser through said zone;

modulating said probe laser at a frequency f; and measuring the change in the output signal transmitted through said fiber to said photodetector.

31. The method of claim 30 where said probe laser light is modulated by a light chopper.

32. The method of claim 30 wherein said probe laser light is modulated by varying the current to the probe laser.

* * * * *